(12) United States Patent
Smith et al.

(10) Patent No.: US 7,497,832 B2
(45) Date of Patent: Mar. 3, 2009

(54) METHOD AND DEVICE FOR MEASURING PERIPHERAL VASCULAR FUNCTION

(75) Inventors: Michael Smith, Oradell, NJ (US); Lloyd Marks, Westfield, NJ (US)

(73) Assignee: Smithmarks, Inc., Ridgefield, NJ (US)

( * ) Notice: Subject to any disclaimer, the term of this patent is extended or adjusted under 35 U.S.C. 154(b) by 678 days.

(21) Appl. No.: 10/759,130

(22) Filed: Jan. 20, 2004

(65) Prior Publication Data

US 2005/0159663 A1    Jul. 21, 2005

(51) Int. Cl.
A61B 5/02    (2006.01)
(52) U.S. Cl. .................. 600/504; 600/481; 600/485
(58) Field of Classification Search ................. 600/485, 600/500–507
See application file for complete search history.

(56) References Cited

U.S. PATENT DOCUMENTS

| 3,796,213 | A | | 3/1974 | Stephens et al. |
| 4,112,491 | A | * | 9/1978 | Bugay .................. 600/502 |
| 4,548,211 | A | * | 10/1985 | Marks .................. 600/507 |
| 4,569,355 | A | * | 2/1986 | Bitterly ................ 600/504 |
| 5,566,677 | A | | 10/1996 | Raines et al. |
| 6,149,587 | A | * | 11/2000 | Raines .................. 600/300 |
| 6,165,130 | A | * | 12/2000 | Chio ..................... 600/485 |
| 6,758,822 | B2 | * | 7/2004 | Romano ................ 600/526 |
| 7,024,244 | B2 | * | 4/2006 | Muhlenberg et al. ... 607/23 |

* cited by examiner

Primary Examiner—Robert L. Nasser, Jr.
Assistant Examiner—Karen E Toth
(74) Attorney, Agent, or Firm—Blank Rome LLP

(57) ABSTRACT

A patient's peripheral pulse volume and blood pressure are measured. The quantities are used to obtain a quantitative measure of peripheral vascular function. The quantitative measure can be one or more of pulsatile limb blood flow, total limb blood flow, limb vascular compliance and limb vascular resistance.

34 Claims, 3 Drawing Sheets

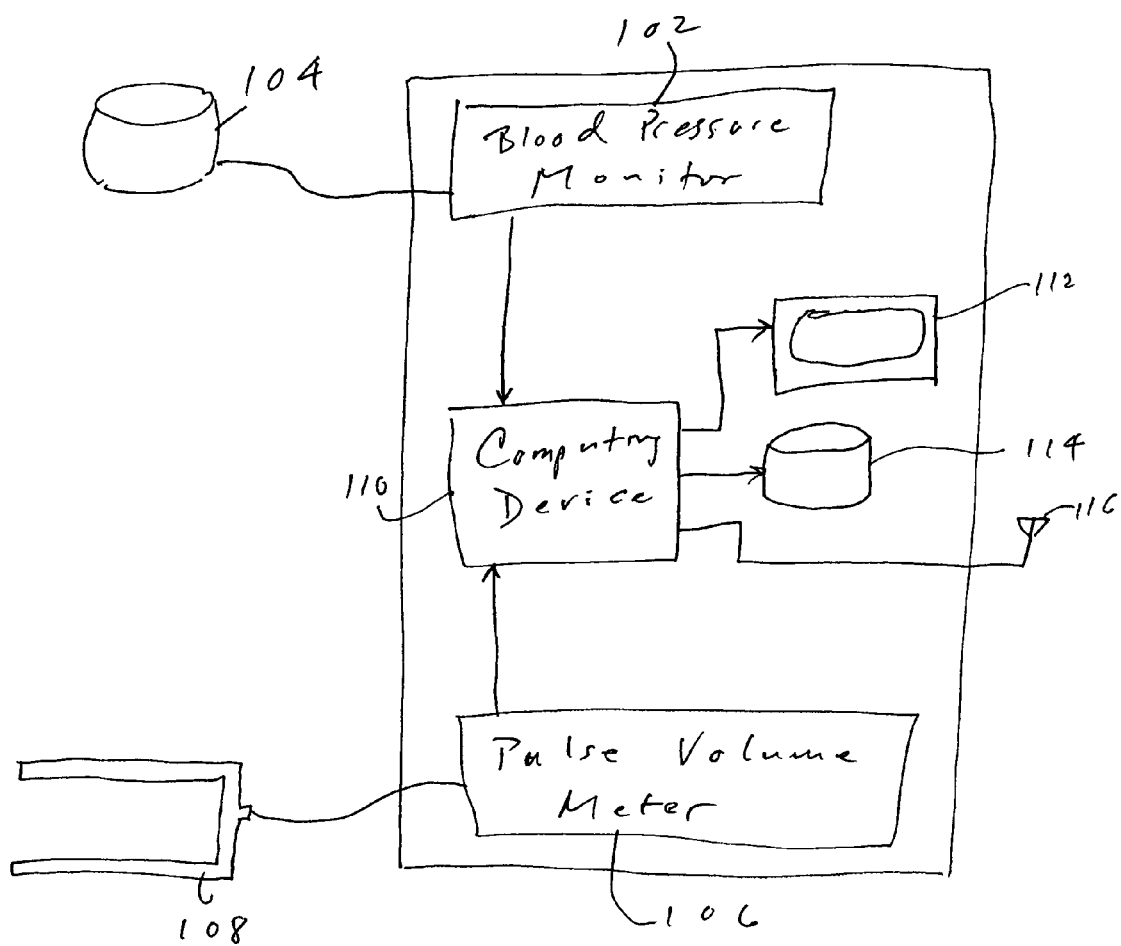

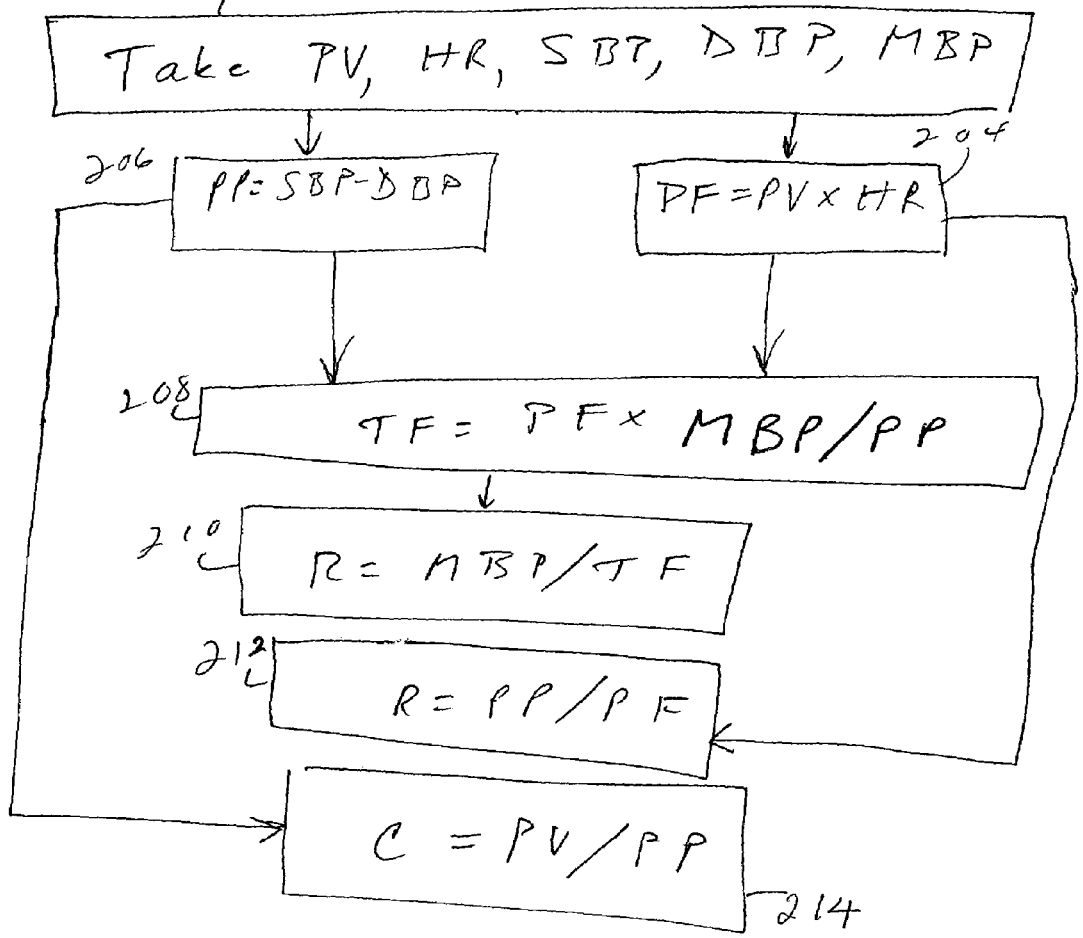

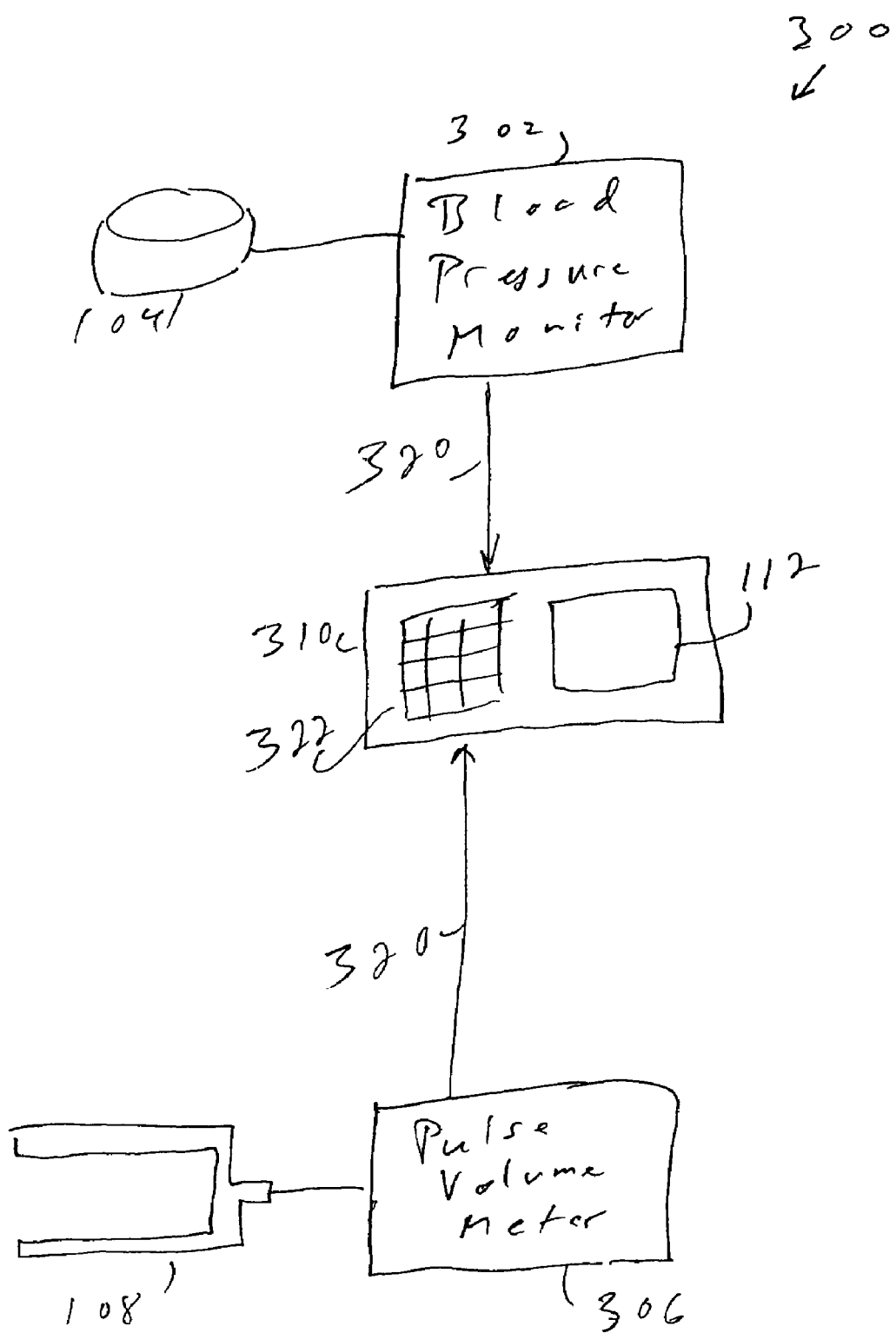

METHOD AND DEVICE FOR MEASURING PERIPHERAL VASCULAR FUNCTION

REFERENCE TO RELATED APPLICATIONS

The following commonly assigned patent applications disclose and claim subject matter related to the subject matter of the present invention: U.S. patent application Ser. No. 10/392,308, filed Mar. 20, 2003, titled "Peripheral impedance plethysmography electrode and system with detection of electrode spacing"; U.S. patent application Ser. No. 10/673,167, filed Sep. 30, 2003, titled "Methods of diagnosis using pulse volume measurement"; and U.S. patent application Ser. No. 10/673,328, filed Sep. 30, 2003, titled "Signal averaging using gating signal obtained from autocorrelation of gating signals." The disclosures of those applications are hereby incorporated by reference in their entireties into the present application.

FIELD OF THE INVENTION

The present invention is directed to the measurement of peripheral vascular function and more particularly to the non-invasive measurement of an objective measure of peripheral vascular function.

DESCRIPTION OF RELATED ART

It is well known in the art to measure various parameters associated with peripheral blood flow. For instance, cuff-type blood pressure monitors are used to measure blood pressure non-invasively. The typical output of a blood pressure monitor includes the following three quantities: systolic blood pressure (SBP), diastolic blood pressure (DBP) and mean blood pressure (MBP).

Also, peripheral impedance (or conductance) plethysmography is a technique for non-invasively measuring peripheral blood flow by measuring peripheral pulse volume per length, which is the small change in the volume of a limb segment occurring within the cardiac cycle. The technique works by obtaining a raw pulse volume analog signal and applying a selective signal averaging algorithm to the raw pulse volume signal. The technique is described in U.S. Pat. No. 4,548,211 to Marks.

Peripheral pulse volume per length (PV) is typically measured in microliters per cm of limb length. That quantity is the volume of blood which enters and leaves, with each cardiac cycle, a limb segment whose borders are defined by the measuring electrodes.

More recently, signal-processed peripheral pulse volume per length measurement has become available. That technique applies selective signal averaging to the peripheral impedance waveform, so that the very small signal can be extracted reproducibly.

However blood pressure and peripheral pulse volume per length have traditionally been measured separately, at separate times, for separate purposes. The two techniques give incomplete information regarding peripheral vascular function. For instance, neither blood pressure nor peripheral pulse volume per length by itself permits a quantitative assessment of any of the following parameters, which are objective measures of peripheral vascular function: pulsatile limb blood flow, total limb blood flow, limb vascular compliance, and limb vascular resistance.

SUMMARY OF THE INVENTION

A need thus exists in the art to provide such objective measurements of peripheral vascular function. It is therefore an object of the invention to provide such objective measurements.

It is another object of the invention to provide such objective measurements by combining measurements of blood pressure and pulse volume to provide more information than either of those quantities provides separately.

It is still another object of the invention to accomplish the above, preferably through non-invasive techniques.

To achieve the above and other objects, the present invention is directed to a method and device for measuring peripheral vascular function. The device combines a pulse volume meter with a blood pressure monitor. The outputs of those two measuring devices are supplied to a computing device that uses the quantities, and optionally also heart rate, to compute various objective quantities representing peripheral vascular function.

BRIEF DESCRIPTION OF THE DRAWINGS

A preferred embodiment of the invention and variations thereof will be described in detail with reference to the drawings, in which:

FIG. 1 is a block diagram showing a device according to the preferred embodiment;

FIG. 2 is a flow chart showing calculations performed in the device of FIG. 1; and FIG. 3 is a block diagram showing a variation of the device of FIG. 1.

DETAILED DESCRIPTION OF THE PREFERRED EMBODIMENT

A preferred embodiment and variations thereof will now be set forth in detail, in which like reference numerals refer to like elements throughout.

FIG. 1 shows a device 100 for measuring peripheral vascular function according to the preferred embodiment. The device 100 includes an integrated blood pressure monitor 102, having a cuff 104 for attachment to a limb, and a pulse volume meter 106, having a peripheral impedance plethysmography electrode 108, for attachment to the limb. The blood pressure monitor 102 and the pulse volume meter 106 operate like those known in the art and will therefore not be described in detail here.

The blood pressure monitor 102 and the pulse volume meter 106 are connected to a computing device 110 to supply their outputs to the computing device. The computing device performs calculations, to be explained below, to provide an objective measure of peripheral vascular function. The computing device can be any device capable of being programmed to perform the calculations to be described below.

The device 100 has one or more of the following outputs for the objective measure. A physician in the field can view the results on a display 112, such as an LED display. The results can be stored in persistent storage 114 (fixed or removable) for later retrieval and analysis. The results can be transmitted from the field to a central location through a radio link 116.

Of course, those skilled in the art will immediately recognize that the device 100 can have other components (e.g., a power supply and a user input) which are not disclosed in detail here. The provision of such components will be well within the skill of those skilled in the art who have reviewed the present disclosure.

The quantities calculated will now be disclosed. One or more of the quantities to be disclosed can be output as needed. Since calculation of a quantity may require calculation of one or more of the other quantities identified, the interrelation among the quantities is shown in the flow chart of FIG. 2. First, the blood pressure monitor 102 and the pulse volume meter 106 are used to take the quantities PV, HR, SBP, DBP and MBP (FIG. 2, step 202).

1. Pulsatile Flow

The product of pulse volume times heart rate HR is the pulsatile component of the volume of blood passing through the limb segment per minute per centimeter of limb length, or the pulsatile flow PF.

$PF=PV \times HR$ (FIG. 2, step 204).

Pulsatile flow can be calculated either as an end in itself or as an intermediate step in the calculation of other quantities.

2. Total Flow

Pulsatile flow occurs during systole. There is a continuous component of the total flow TF which occurs during systole and diastole. Since vascular resistance is approximately constant (constant to the first order), the ratio of pulsatile flow to total flow can be approximated as the ratio of the pulse pressure to the mean blood pressure. Pulse pressure PP is the difference between systolic and diastolic pressure. Total flow may thus be calculated as follows:

$PP=SBP-DBP$ (FIG. 2, step 206);

$TF=PF \times MBP/PP$ (FIG. 2, step 208).

3. Vascular Resistance

Vascular resistance, R, is simply the mean arterial pressure divided by the total flow:

$R=MBP/TF$ (FIG. 2, step 210).

Alternatively, R can be calculated as follows:

$R=PP/PF$ (FIG. 2, step 212).

4. Vascular Compliance

Vascular compliance, C, is the increase in volume caused by a known increase in blood pressure. That parameter can be computed as follows:

$C=PV/PP$ (FIG. 2, step 214).

One, more, or all of the above quantities can form the output of the computing device 110.

A variation of the preferred embodiment will be explained with reference to FIG. 3. In the system 300 of FIG. 3, the blood pressure monitor 302, the pulse volume meter 306 and the computing device 310 are provided as separate devices. The outputs of the blood pressure monitor 302 and the pulse volume meter 306 can be supplied to the computing device 310 either automatically, through connections (wireline or wireless) 320, or manually, through a keypad 322. Otherwise, the structure and functionality are the same as in the device 100 of FIG. 1.

While a preferred embodiment and variations thereof have been set forth in detail above, those skilled in the art who have reviewed the present disclosure will readily appreciate that other embodiments can be realized within the scope of the invention. For example, any suitable hardware for performing the required measurements and calculations can be used. Also, other quantities representing peripheral vascular function can be developed and calculated. Further, the plethysmographic techniques disclosed and claimed in commonly assigned U.S. patent application Ser. No. 10/392,308, filed Mar. 20, 2003, titled "Peripheral impedance plethysmography electrode and system with detection of electrode spacing," and Ser. No. 10/673,328, filed Sep. 30, 2003, titled "Signal averaging using gating signal obtained from autocorrelation of gating signals," can be used in the present invention. Therefore, the present invention should be construed as limited only by the appended claims.

We claim:

1. A method for quantitatively assessing a peripheral vascular function in a limb of a patient, the method comprising:
   (a) measuring a peripheral pulse volume per length PV in the limb of the patient;
   (b) measuring a blood pressure of the patient; and
   (c) calculating a quantity that is a mathematical function of the peripheral vascular function in the limb, using the peripheral pulse volume PV measured in step (a) and the blood pressure measured in step (b).

2. The method of claim 1, wherein step (b) comprises:
   (i) measuring a diastolic blood pressure DBP of the patient;
   (ii) measuring a systolic blood pressure SBP of the patient; and
   (iii) calculating a pulse pressure PP of the patient as PP=SBP−DBP.

3. The method of claim 2, further comprising measuring a heart rate HR of the patient, and wherein step (c) comprises calculating the quantity also using the heart rate HR.

4. The method of claim 3, wherein step (c) comprises calculating a pulsatile flow PF as PF=PV×HR.

5. The method of claim 4, wherein step (c) further comprises calculating a vascular resistance R as PP/PF.

6. The method of claim 4, wherein:
   step (b) further comprises calculating a mean blood pressure MBP; and
   step (c) further comprises calculating a total flow TF as TF=PF ×MBP/PP.

7. The method of claim 6, wherein step (c) further comprises calculating a vascular resistance R as R=MBP/TF.

8. The method of claim 2, wherein step (c) comprises calculating a vascular compliance C as C=PV/PP.

9. The method of claim 1, further comprising controlling a display to display the quantity calculated in step (c).

10. The method of claim 1, further comprising controlling a storage device to store the quantity calculated in step (c) for later review.

11. The method of claim 1, further comprising transmitting the quantity calculated in step (c) over a communication link to a remote location for review.

12. The method of claim 1, wherein steps (a), (b) and (c) are performed using an integrated device.

13. The method of claim 1, wherein:
   step (a) is performed using a pulse volume meter;
   step (b) is performed using a blood pressure monitor which is provided separately from the pulse volume meter; and
   step (c) is performed using a computing device which is provided separately from the pulse volume meter and the blood pressure monitor.

14. The method of claim 13, wherein the peripheral pulse volume and the blood pressure are input automatically into the computing device.

15. The method of claim 13, wherein the peripheral pulse volume and the blood pressure are input manually into the computing device.

16. A system for quantitatively assessing a peripheral vascular function in a limb of a patient, the system comprising:

a pulse volume meter for measuring a peripheral pulse volume per length PV in the limb of the patient;

a blood pressure monitor for measuring a blood pressure of the patient; and a computing device for receiving the peripheral pulse volume and the blood pressure and for calculating a quantity that is a mathematical function of the peripheral vascular function in the limb, using the peripheral pulse volume and the blood pressure.

17. The system of claim 16, wherein the blood pressure monitor measures a diastolic blood pressure DBP of the patient and a systolic blood pressure SBP of the patient and calculates a pulse pressure PP of the patient as PP=SBP−DBP.

18. The system of claim 17, wherein the computing device also receives a heart rate HR of the patient and calculates the quantity also using the heart rate HR.

19. The system of claim 18, wherein the computing device also calculates a pulsatile flow PF as PF=PV×HR.

20. The system of claim 19, wherein the computing device also calculates a vascular resistance R as PP/PF.

21. The system of claim 19, wherein:
the blood pressure monitor calculates a mean blood pressure MBP; and
the computing device also calculates a total flow TF as TF=PF×MBP/PP.

22. The system of claim 21, wherein the computing device calculates a vascular resistance R as R=MBP/TF.

23. The system of claim 17, wherein the computing device calculates a vascular compliance C as C=PV/PP.

24. The system of claim 16, wherein the computing device comprises a display for displaying the quantity calculated by the computing device.

25. The system of claim 16, wherein the computing device comprises a storage device for storing the quantity calculated by the computing device.

26. The system of claim 16, wherein the computing device comprises a communication link for transmitting the quantity calculated by the computing device over a communication link to a remote location for review.

27. The system of claim 16, wherein the pulse volume meter, the blood pressure monitor and the computing device are comprised in an integrated device.

28. The system of claim 16, wherein the pulse volume meter, the blood pressure monitor and the computing device are separate devices.

29. The system of claim 28, wherein the pulse volume meter, the blood pressure monitor and the computing device are in communication with one another such that the peripheral pulse volume and the blood pressure are input automatically into the computing device.

30. The system of claim 28, wherein the peripheral pulse volume and the blood pressure are input manually into the computing device.

31. The method of claim 1, wherein the mathematical function is selected from the group consisting of pulsatile limb blood flow, total limb blood flow, limb vascular compliance, and limb vascular resistance.

32. The system of claim 16, wherein the mathematical function is selected from the group consisting of pulsatile limb blood flow, total limb blood flow, limb vascular compliance, and limb vascular resistance.

33. A method for quantitatively assessing a peripheral vascular function in a limb of a patient, the method comprising:
(a) measuring a peripheral pulse volume per length PV in the limb of the patient;
(b) measuring a blood pressure and a heart rate HR of the patient; and
(c) calculating a quantity representing the peripheral vascular function in the limb, using the peripheral pulse volume PV measured in step (a) and the blood pressure measured in step (b), wherein step (c) comprises calculating a pulsatile flow PF as PF=PV×HR.

34. A system for quantitatively assessing a peripheral vascular function in a limb of a patient, the system comprising:
a pulse volume meter for measuring a peripheral pulse volume per length PV in the limb of the patient;
a blood pressure and heart rate monitor for measuring a blood pressure and a heart rate HR of the patient; and
a computing device for receiving the peripheral pulse volume and the blood pressure and for calculating a quantity representing the peripheral vascular function in the limb, using the peripheral pulse volume and the blood pressure, wherein the computing device also calculates a pulsatile flow PF as PF=PV×HR.

* * * * *